United States Patent [19]

Sugihara

[11] Patent Number: 5,699,155
[45] Date of Patent: Dec. 16, 1997

[54] EMISSION SPECTRAL ANALYSIS METHOD AND INSTRUMENT THEREFOR

[75] Inventor: Takashi Sugihara, Chiba, Japan

[73] Assignees: Kawasaki Steel Corporation; Shimadzu Corporation, both of Japan

[21] Appl. No.: 581,561

[22] PCT Filed: Jul. 25, 1994

[86] PCT No.: PCT/JP94/01216
  § 371 Date: Jan. 29, 1996
  § 102(e) Date: Jan. 29, 1996

[87] PCT Pub. No.: WO95/03536
  PCT Pub. Date: Feb. 2, 1995

[30] Foreign Application Priority Data

Jul. 26, 1993 [JP] Japan .................. HEI 5-183953
May 31, 1994 [JP] Japan .................. HEI 6-118712

[51] Int. Cl.$^6$ ............................. G01N 21/67
[52] U.S. Cl. ............................. 356/313
[58] Field of Search ............................. 356/56, 313

[56] References Cited

U.S. PATENT DOCUMENTS 4,289,402  9/1981  Teubner ................... 356/313
4,544,270  10/1985  Berstermann et al. ................. 356/313
4,571,074  2/1986  Thevenon ................... 356/51

FOREIGN PATENT DOCUMENTS 0398462  11/1990  European Pat. Off. ............ 356/313
62-201048  12/1987  Japan .
1-274043  11/1989  Japan .

*Primary Examiner*—F. L. Evans

[57] ABSTRACT

An improved emission spectral analysis method and apparatus for analyzing a sample by causing discharge and light emission between the sample and the counter electrode, spectroscopically dispersing the spectral lines peculiar to the elements, and measuring the wavelength and intensity of each spectral line. The discharge is caused in such a way that the surface of the sample facing the counter electrode is made to almost parallel to the light gathering axis of a spectroscope. Consequently, spectral lines which are not affected by the light of the sample itself and vapor can be gathered into the spectroscope and the background variation of the spectral lines can be reduced. In addition, light is gathered in a plurality of directions, so that the analysis accuracy can be improved and the lower determination limit can be expanded.

11 Claims, 4 Drawing Sheets

EMISSION SPECTRAL ANALYSIS METHOD AND INSTRUMENT THEREFOR

TECHNICAL FIELD

The present invention relates to an emission spectral analysis method and an instrument therefor adapted to perform measurement of the kinds and contents of the respective elements contained in an analytical sample.

BACKGROUND ART

In general, according to the emission spectral analysis using a spark discharge or an arc discharge, the spark discharge or the arc discharge is conducted between a sample and a counter electrode so that a part of the sample is vaporized by the discharge energy to excite the vaporized atoms and ions. A transition of these atoms and ions into a lower energy level causes emanation of peculiar spectral lines each having an intensity according to the density of the associated element.

At the place where the spectral lines emanated, there is provided a state of a continuous spectral line in which peculiar spectral lines on the respective elements and scattered light are mixed. The continuous spectral line is introduced into a spectroscope to be spectroscopically dispersed by a diffraction grating installed in the spectroscope, so that peculiar spectral lines on the elements of interest in measurement are detected, respectively. A kind of each of the elements contained in a sample is determined on the basis of the wavelength position thus obtained, whereas a content of each of the elements is determined on the basis of intensity of the spectral line.

Usually, such a detection is performed by detectors (photomultipliers) each of which is disposed on an optimum basis to meet the wavelength of the corresponding spectral line for each element in the spectroscope. Finally, intensity of the detected spectral line, or quantity is subjected to a photometric processing in the form of emission intensity, so that arithmetic on the respective element contents are performed by a computer.

Such an emission spectral analysis instrument comprises: a counter electrode for causing an arc discharge or a spark discharge; an emission stand for holding a sample at a position where the sample is located over said counter electrode; a spectroscope for receiving and spectroscopically dispersing spectral lines emanated from the sample held on said emission stand; and photometric equipment adapted to perform measurement of the kinds and contents of the elements contained in the sample on the basis of the wavelength position thus obtained by the spectroscope and intensity of the spectral lines.

The emission stand is provided with a sample holding member for holding the sample at a position where the sample is located over a tip of the counter electrode. A discharge is performed 1–1000 times/sec. between the surface of the sample and the counter electrode so that atoms and ions, as conversion of the constituent elements of the sample, are excited. A transition of these atoms and ions into a lower energy level causes emanation of peculiar spectral lines each corresponding to the associated element. After spectroscopically dispersing through the spectroscope, kinds and contents of the elements contained in the sample are measured on the basis of the wavelength and intensity of the spectral lines.

According to a discharge type of emission spectral analyzer on the market, since the spectral lines having not more than 200 nm of wavelength are absorbed into air and thus cannot be measured, an atmosphere of inert gas, usually, Ar, He and the like, is provided in the space between an emission unit in which a sample is accommodated and a spectroscope, whereas a vacuum state is provided, usually using a vacuum pump, for the inside of the spectroscope.

The emission stand for setting samples is made of metal having a thickness of 2 mm–3 mm or ceramics in order to provide a suitable strength for holding the samples and the counter electrode for discharge. It happens that this thickness occupies over half of a distance 3 mm–6 mm between the electrode and the sample. Further, there exists vapor emanated from the sample due to a spark discharge. Consequently, an effective portion available for an analysis is merely of the order of 1 mm–2 mm. In order to relieve obstruction of introduction of the emanated spectral lines into a spectroscope by the thickness of a sample holding plate of the emission stand, a sample holding surface of the conventional emission stand is inclined with respect to the light gathering axis of the spectroscope (cf. EMISSION SPECTRAL ANALYSIS METHOD, page 101, Sep. 20, 1967, issued by KYORITSU PUBLICATION CO., LTD.). This taper angle is usually 12°–15°.

As mentioned above, the sample holding section of the emission stand of the conventional emission spectral analyzing apparatus is inclined with respect to the light gathering axis of the spectroscope. Thus, it is considered that:

(a) light of the sample itself heated by the spark discharge is gathered into the spectroscope, and (b) the height of the vapor cloud emanated by the spark discharge is about 1 mm from the sample. The spectral lines, which are absorbed or scattered by the vapor cloud, in other words, which are subjected to interference of the vapor cloud, are gathered into the spectroscope.

As a result of the above-mentioned (a) and (b), the background of the spectral lines gathered into the spectroscope is varied. This causes degradation of analysis accuracy. For instance, providing a high index of cleanliness of steel needs high analysis accuracy. However, the structure of the emission stand of the conventional emission spectral analyzing apparatus is associated with limit, in analysis accuracy.

Further, an emission spectral analyzer on the market is simply provided with a piece of spectroscope for directly gathering discharge light. According to such an analyzer, there are provided a plurality of detectors which are arranged in the spectroscope by a corresponding number of elements of interest in measurement in order Of magnitude of wavelength, whereas there is provided a single diffraction grating (For example, Shimadzu Corporation Catalog, Shimadzu Vacuum Type of Emission Analyzing Apparatus, PDA-5017, PDA-1017, EMISSION SPECTROMETER). The reason for this is the fact that the sample holding section of the emission stand as mentioned above is inclined with respect to the light gathering axis of the spectroscope. That is, because the optimum gathering direction will be restricted to one direction since the sample holding section is inclined. And, usually, there is used a diffraction grating having the focal length of 500 mm–1000 mm and the dispersion of 0.3–0.7 nm/mm. The optimum range of the optimum wavelength of the spectral lines which can be measured is given by the wavelength of 160 nm to 600 nm among the wavelengths shown in TABLE 1.

In a case where a steel material is analyzed with the emission spectral analyzer on the market, usually, the elements of interest in analysis are over 20 elements such as C, Si, Mn, P, S, Al, Cu, Ni, Cr, Mo, V, Nb, Ti, B, Ca, Fe, Sb, Co, As, Sn and the like, and these elements may be simultaneously analyzed in short time. In addition, the measuring spectral lines of these elements are given, as shown in TABLE 1 by way of example, over the wide range such as near 160 nm on element C through near 400 on elements Al and Ca to 600 nm–700 nm on elements Na and K.

TABLE 1

| Elements | Wavelengths (nm) |
|---|---|
| H | 121.6 |
| O | 130.2 |
| N | 149.2 |
| C | 156.1 |
| C | 165.8 |
| P | 178.3 |
| S | 180.7 |
| Mo | 202.0 |
| Si | 212.4 |
| Cu | 224.2 |
| Ni | 227.7 |
| Mn | 290.0 |
| Cr | 298.9 |
| V | 311.0 |
| Nb | 319.5 |
| Al | 394.4 |
| Pb | 410.3 |
| Na | 589.0 |
| Li | 607.8 |
| K | 766.5 |

These elements are able to be measured through a single spectroscope. However, among those elements there are some ones which will be affected by overlap of the spectral line of another element coming close to the inherent spectral line of the element of interest in measurement. Such elements will be decreased in resolution of the spectral line and thus has poor analysis accuracy.

This is a serious problem for analysis engineers in view of the current situation that it is required to provide a high index of cleanliness of steel materials and, for analysis needs, it is required that the lower determination limit is expanded. With respect to the influence of overlap of the spectral line of another element as mentioned above, it is possible to decrease such influence by providing higher resolution of the diffraction grating and in addition providing improved dispersion (nm/mm: a range of wavelength per 1 mm on the detection portion). However, implementation of this matter with a single spectroscope causes such an obstacle that the bulk of the spectroscope becomes too vast. It is necessary for the spectroscope to evacuate the inside thereof, and also to improve airtightness for the purpose of reduction of absorption time to a vacuum and maintaining the vacuum state. From the point of view as mentioned above, it is not preferable to provide a vast bulk.

DISCLOSURE OF THE INVENTION

An object of the present invention is to provide an emission spectral analysis method capable of improving the analysis accuracy, and also of expanding the lower limit in determination of the respective elements, that is, the lower determination limit.

Another object of the present invention is to provide an emission spectral analysis instrument capable of improving the analysis accuracy in comparison with the prior art, which instrument can be preferably adopted to putting into practice the above-mentioned method.

According to the present invention, there is provided an emission spectral analysis method in which a discharge is caused between a sample and a counter electrode to emit light, the light thus emanated is gathered and spectral lines peculiar to respective component elements included therein are spectroscopically dispersed, and wavelength and intensity on each of the inherent spectral lines are measured, characterized in that the discharge light is gathered in such a manner that a surface of the sample does not come within the range of a spectroscope.

Further, according to the present invention, there is provided an emission spectral analysis method as described above, wherein a discharge is carried out keeping a surface of the sample facing the counter electrode approximately parallel to a light gathering axis of a spectroscope, and light gathering is conducted from a plurality of directions. It is preferable that the angle of the surface of the sample facing the counter electrode with respect to the light gathering axis of a spectroscope is desirably not more than 5°, more desirably not more than 1°, further more desirably substantially 0°. In this case, it is preferable that the light gathering is conducted on each of at least two kinds of wavelength area selected from a group consisting of (a) a wavelength area of an ultraviolet rays region less than 100 nm–160 nm, (b) a wavelength area of a visible rays region of 160 nm–600 nm, and (c) a wavelength area of an infrared rays region over 600 nm, a spectroscopical dispersing is conducted, and a measurement is conducted. Further, it is preferable that messages as to intensity of spectral lines peculiar to respective component elements obtained through light gathering from said plurality of directions are simultaneously measured and then converted into contents, and in addition correction of coexisting elements is also simultaneously performed. Furthermore, if the discharge section is partitioned into a multi-layer by a slit or the like so as to gather light from a plurality of directions, it is possible to detect separately heavy elements and light elements with accuracy. It is desirable that the light gathering axis is made to be a straight line.

According to the present invention, there is further provided an emission spectral analysis apparatus comprising an emission stand, a discharge device, a spectroscope, a photometric device and a content computer, characterized in that a surface of the sample facing the counter electrode is substantially parallel to a light gathering axis of a spectroscope. In this case, it is preferable that the angle of the surface of the sample facing the counter electrode with respect to the light gathering axis is desirably not more than 5°, more desirably not more than 1°, further more desirably substantially 0°.

It is preferable that a sample holding section, which comes in contact with a sample, is constituted of a flat plate having a thickness of not less than one sixth but not more than one third of the length between the sample and a tip of a counter electrode. That is, assuming that the thickness of the flat plate is given by t(mm) and the length between the sample and the tip of the counter electrode is given by L (mm), it may be expressed by $L/3 \geq t \geq L/6$.

Further, it is preferable that the sample holding section is made of ceramics, for example, metal or AlN, and more desirably, is made of ceramics such as AlN.

Furthermore, in a case where the sample holding section of the emission stand is made of ceramics, it is preferable that the sample holding surface is provided with a metallic coating with a metal excellent in conductivity, for example, tungsten or the like. As a coating method, there are considered several ways, such as an electrolytic plating process, a dipping process in which an object is dipped into the melted plating material, and a vacuum evaporation process.

As another apparatus according to the present invention, there is provided an emission spectral analysis apparatus comprising an emission stand, a discharge device, a spectroscope, a photometric device and a content computer, characterized in that the apparatus comprises: a sample holding section in which inclination of a light gathering axis of the spectroscope with respect to a sample holding surface facing said counter electrode is below 5°; and a plurality of spectroscopes each adapted for spectroscopically dispersing said emission on a diffraction basis. In this case, it is preferable that the angle of the surface of the sample facing the counter electrode with respect to the light gathering axis of a spectroscope is desirably not more than 5°, more desirably not more than 1°, further more desirably substantially 0°. It is preferable that said apparatus is provided with two or more spectroscopes corresponding to a measurement of spectral lines of two or more wavelength areas selected from a group consisting of (a) a wavelength area of an ultraviolet rays region less than 100 nm–160 nm, (b) a wavelength area of a visible rays region of 160 nm–600 nm, and (c) a wavelength area of an infrared rays region over 600 nm. Further, it is desirable that each of the plurality of spectroscopes is so arranged that a slit is provided on a discharge section to hierarchically gather light.

With respect to the sample of interest in analysis for the emission spectral analysis method and apparatus according to the present invention, it is acceptable that adopted are any metallic materials, for example, iron and steel materials such as low-alloy steel, for instance, cast iron, pig iron and steel, and high-alloy steel, for instance, stainless steel; aluminium alloy; and copper alloy.

BEST MODE FOR CARRYING OUT THE INVENTION

Figure 6:
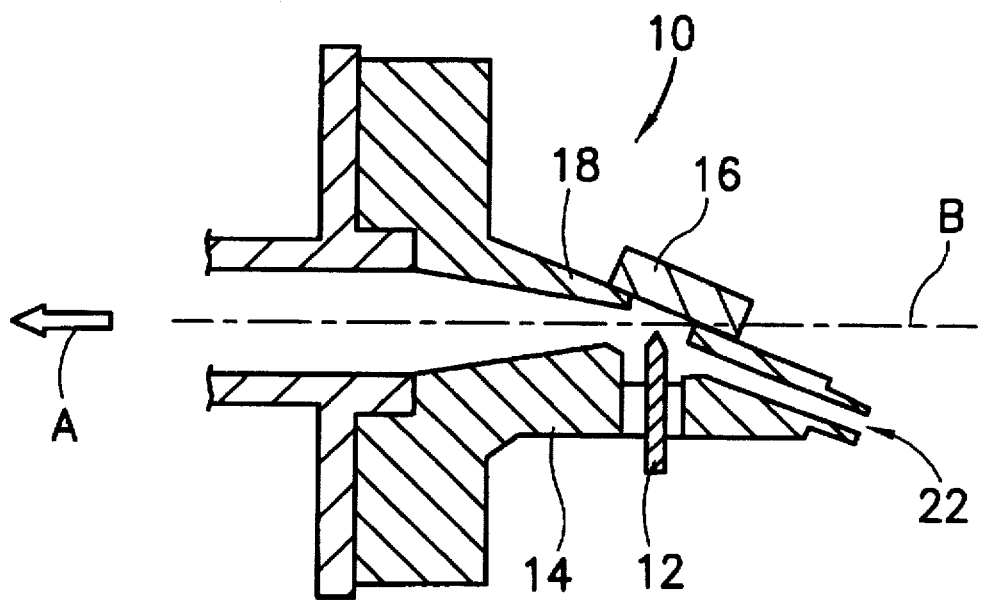
FIG. 6 is an overall view of an emission stand having an inclined sample surface according to the prior art.
Figure 7:
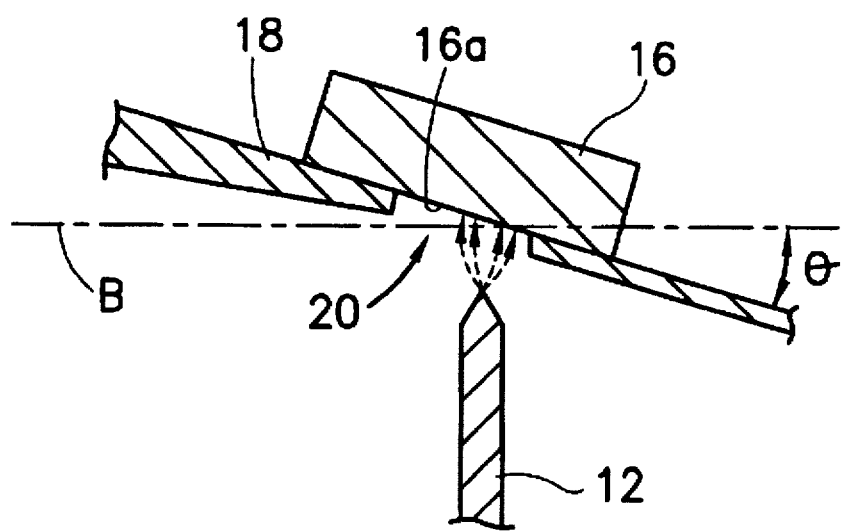
FIG. 7 is a vertical sectional view showing details of a sample holder section having an inclined sample surface.

FIG. 6 is a sectional view showing the conventional emission stand, and FIG. 7 is the sectional view showing with enlargement a spark discharge section of the emission stand shown in FIG. 6.

An emission stand 10 comprises a bottom wall on which a counter electrode 12 made of tungsten or silver, and a sample holder section 18 for holding a sample 16 with an inclination at a position where the sample 16 is located over against the tip of the counter electrode 12. The sample holder section 18 is provided with an aperture 20 which is be covered by the sample. A discharge is conducted in a certain cycle (1–1000 times/sec) to a portion 16a facing the aperture 20 of the sample 16, whereby the portion 16a of the sample 16 is vaporized to generate a vapor cloud, and the constituent elements of the sample 16 are converted into atoms and ions and then removed. Transition of those atoms and ions into a lower energy level causes generation of spectral lines each corresponding to the associated element. The spectral lines are generated for every discharge from the sample 16 toward the inside of the emission stand. Only the spectral lines directed (direction shown with an arrow A) to a spectroscope (not illustrated) disposed at the left side of the sheet surface of FIG. 6 are gathered by the spectroscope and then dispersed. Thereafter, kinds and contents of the elements contained in the sample are measured on the basis of the wavelength position and intensity of the spectral lines which are obtained through the spectroscope. When the wavelength of the spectral lines generated from the sample 16 is less than 200 nm, the spectral lines are absorbed in air and thus cannot be gathered by the spectroscope. Hence, the space between the discharge section and the spectroscope is filled with inert gas such as Ar gas, He gas and the like to provide an inert gas atmosphere, the inside of the spectroscope is brought into a vacuum state usually using the vacuum pump, and the inert gas is supplied from a gas supplying inlet 22 to replace at a certain flow velocity the inert gas in space between the discharge section and the spectroscope. Since it is necessary for the emission stand 10 in which the sample is held to have conductivity and strength, the emission stand 10 is made of, usually, metal or ceramics. The sample holder section 18 has thickness of 2–3 mm, since it is necessary for the sample holder section 18 to have strength sufficient for holding the sample 16 thereon. As shown in FIG. 7, the thickness of 2–3 mm of the sample holder section 18 is about half of the distance (3–6 mm) between the tip of the counter electrode 12 and the sample 16. This prevents the spectral lines emanated from the sample 16 from travelling toward the spectroscope. For this reason, as shown in FIG. 7, the sample holder section 18 is formed with inclination of angle θ with respect to the light gathering axis B of the spectroscope so that the spectral lines emanating from the sample 16 travel toward the spectroscope as need as possible.

For the reasons described above, light of the heated sample itself is gathered into the spectroscope, and the spectral lines subjected to interference of vapor cloud are gathered into the spectroscope. These cause the background to be varied. Thus, it would be impossible to improve the analysis accuracy.

According to the present invention, there is provided an emission spectral analysis method in which a discharge is caused between a sample and a counter electrode to emit light, the light thus emanated is gathered and spectral lines peculiar to respective component elements included therein are spectroscopically dispersed, and the wavelength and intensity on each of the inherent spectral lines are measured, wherein only the discharge light is gathered in such a manner that a surface of the sample does not come within the range of a spectroscope. This feature makes it possible to reduce the background variation of the spectral lines gathered into the spectroscope, thereby improving analysis accuracy.

Further, according to the present invention, a discharge is carried out keeping a surface of the sample facing the counter electrode approximately parallel to a light gathering axis of a spectroscope, and light gathering is conducted from a plurality of directions. As a result, the background variation of the spectral lines to be measured after diffraction by the spectroscopes is reduced, thereby improving the analysis accuracy of the elements and in addition expanding the lower determination limit. It is preferable that the angle θ of the surface of the sample facing the counter electrode with respect to the light gathering axis of a spectroscope is desirably not more than 5°, more desirably not more than 1°, further more desirably substantially 0°. Further, according to the present invention, messages as to intensity of spectral lines peculiar to respective component elements obtained through light gathering from said plurality of directions are simultaneously measured and then converted into contents, and in addition correction of coexisting elements is also simultaneously performed. This feature makes it possible to perform the simultaneous determination of the other elements, and in addition to contribute to a reduction of analysis time, the labor-saving for the analysis work, and a reduction of analysis cost. Furthermore, if the light gathering axis is made to be a straight line, but not refracting the gathered light by a reflecting mirror or a glass fiber, it is possible to contribute to stabilizing images.

In an emission spectral analysis apparatus which may preferably put the method according to the present invention into practice, a surface of the sample facing the counter electrode is substantially parallel to a light gathering axis of a spectroscope. Thus, even if the sample placed on the sample holding surface is heated through a discharge to emit light, it is possible to prevent light emitted from the sample itself from being gathered into the spectroscope, since a light axis of the light emitted from the sample itself is substantially perpendicular to the light gathering axis of the spectroscope. In this case, it is preferable that the angle of the sample holding surface with respect to the light gathering axis is desirably not more than 5°, more desirably not more than 1°, further more desirably substantially 0°.

The reason why the configuration of the sample holding section is restricted will be explained.

Assuming that the length between the sample held by the sample holding section and the tip of the counter electrode is given by L, if thickness t of the flat plate of the sample holding section is given with less than L/6, the spectral lines emanated due to excitation of the sample will be absorbed or scattered by the vapor cloud so that the spectroscope gathers many spectral lines which are affected by the vapor cloud. This causes the background variation to be expanded. Thus, it is difficult to improve measurement accuracy.

On the other hand, if thickness t of the flat plate is given with more than L/3, the area for introducing into the spectroscope the spectral lines generated owing to excitation of the sample narrows and then this prevents the spectral lines from being introduced into the spectroscope. On the other hand, if the sample holding section is constituted of a flat plate having thickness of L/6 to L/3, it is possible to gather many spectral lines which are not affected by the vapor cloud, thereby reducing the background variation and in addition gathering into the spectroscope the spectral lines generated owing to excitation of the sample. Thus, it is possible to improve analysis accuracy and in addition to expand the lower determination limit.

Further, if the sample holding section is made of ceramics, for example, AlN and the like, it is possible to improve strength, thereby reducing strain due to heat. This feature makes it possible to prevent deterioration in the analysis accuracy due to deformation of the sample holding section.

Furthermore, if the sample holding surface of the emission stand is provided with a metallic coating with a metal excellent in conductivity, for example, tungsten or the like, it is possible to improve the conductivity between the sample and the sample holding section, thereby obtaining the stabilized spark discharge.

An apparatus according to the present invention comprises a sample holding section in which a light gathering axis of a spectroscope is substantially parallel to a sample holding surface facing a counter electrode, and a plurality of spectroscopes each adapted for spectroscopically dispersing the emission on a diffraction basis. It is preferable that the plurality of spectroscopes correspond to measurement of spectral lines of wavelength areas involved in (a) a wavelength area of an ultraviolet rays region less than 100 nm–160 nm, (b) a wavelength area of a visible rays region of 160 nm–600 nm, and (c) a wavelength area of an infrared rays region over 600 nm. In this case, it is preferable that the angle of the surface of the sample facing the counter electrode with respect to the light gathering axis of a spectroscope is desirably not more than 5°, more desirably not more than 1°, further more desirably substantially 0°.

In this manner, it becomes possible to analyze the lower determination limit of all of the elements in the order of 1 ppm. Specifically, with respect to the analysis of elements, such as H, O and N, which are not more than 150 nm in wavelength of a spectral line, hitherto, an emission spectral analysis method is not adopted because of lack of the analysis accuracy. However, according to the present invention, it becomes possible to determine these elements also with accuracy. Further, the emission spectral analysis method and apparatus according to the present invention make it possible to perform the determination analysis of a very small amount of elements C and S less than 10 ppm. Thus, there is no need to depend on the conventional combustion method which will take much time, great expense, and a great deal of labor.

EXAMPLE 1, COMPARISON 1

Hereinafter, a preferred embodiment of an emission spectral analyzer according to the present invention will be described with reference to the accompanying drawing.

Figure 1:
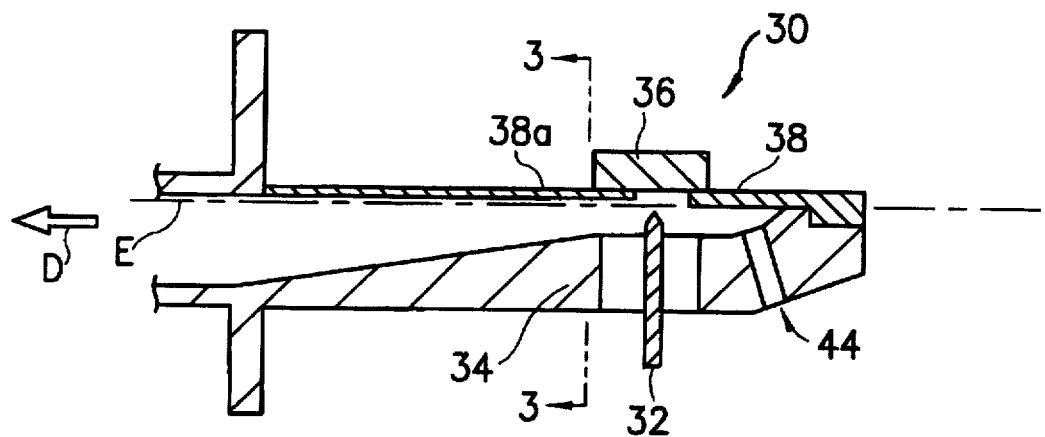
FIG. 1 is a sectional view of an emission stand, by way of example, of an emission spectral analyzer according to the present invention.
Figure 2:
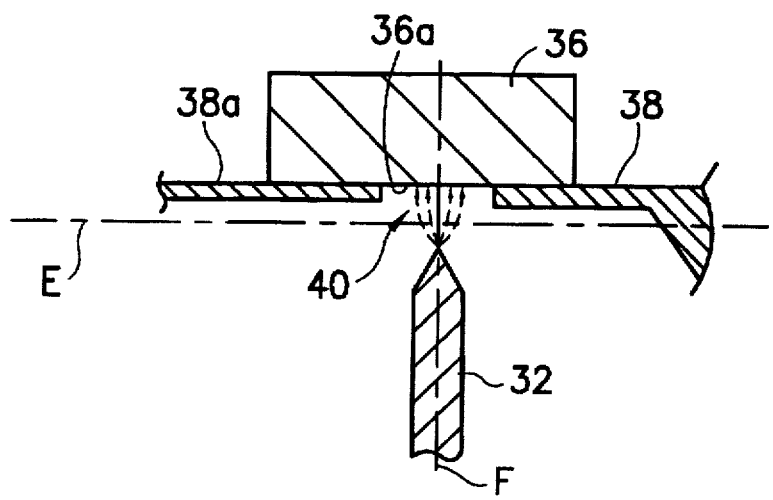
FIG. 2 is a sectional view showing with enlargement a spark discharge section of the emission stand shown in FIG. 1.
Figure 3:
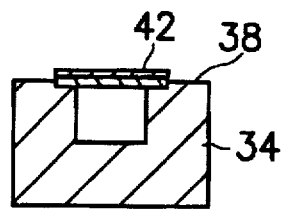
FIG. 3 is a sectional view taken along the line 3—3 of FIG. 1.

FIG. 1 is a sectional view of an emission stand of an emission spectral analyzer; FIG. 2 is a sectional view showing with enlargement a spark discharge section of the emission stand shown in FIG. 1; and FIG. 3 is a sectional view taken along the line 3—3 of FIG. 1.

The emission spectral analyzer is provided with a spectroscope (not illustrated) for gathering and spectroscopically dispersing spectral lines generated from a sample, and a photometric device (not illustrated) for measuring kinds and contents of elements contained in the sample on the basis of wavelength position and intensity of spectral lines obtained through the spectroscope. These equipments are the same as the conventional ones.

An emission stand 30 comprises a bottom wall 34 on which a counter electrode 32 made of tungsten or silver, and a sample holder section 38 for holding a sample 36 at a position where the sample 36 is located over against the tip of the counter electrode 32. The sample holder section 38 is provided with an aperture 40 which will be covered by the sample held. The sample holder section 38 is constituted of a flat plate having thickness of about four eighteenths of the length between the sample 36 and the tip of the counter electrode 32. Since the sample holder section 38 needs strength, it is made of ceramics such as AlN or metal. In order to ensure excellent conductivity, a sample holding surface 38a is formed with a metallic coating layer 42 with metal excellent in conductivity, for example, tungsten. The sample holding surface 38a is made to be parallel with the light gathering axis E of a spectroscope (not illustrated). A central axis F of the counter electrode 32 in the longitudinal direction is made perpendicular to the light gathering axis E of the spectroscope.

To analyze the sample 36, a certain amount of inert gas is fed from an inert gas introducing inlet 44, and a voltage is applied to a gap between the sample 36 and the counter electrode 32 to perform a spark discharge, thereby exciting the sample. The spectral lines emanated due to the excitation are gathered into the spectroscope to measure kinds and contents of the elements contained in the sample.

As mentioned above, since the sample holding surface 38a of the sample holder section 38 is parallel to the light gathering axis E of the spectroscope, the light axis of light emitted from the sample 36 itself is substantially perpendicular to the light axis of light received by the spectroscope, even if the sample 36 placed on the sample holding surface 38a is heated by discharge and the sample 36 itself emanates light. Consequently, it does not almost happen that the spectroscope receives light emitted from the sample 36 itself. Thus, it is possible to reduce the background variation of the spectral lines gathered into the spectroscope. Further, as mentioned above, since the plate thickness of the sample holder section 38 is about four eighteenth of a length between the sample 36 and the tip of the counter electrode 32, it is possible to gather into the spectroscope many spectral lines which are independent of the vapor cloud, so that the background variation can be reduced, thereby gathering into the spectroscope many spectral lines which emanate due to excitation of the sample. Accordingly, it is possible to improve the analysis accuracy, and in addition to expand the lower determination limit.

As mentioned above, according to the emission spectral analyzer of the present invention, it is so arranged that the light gathering axis of the spectroscope is substantially parallel to the sample holding surface, and thus light emitted from the sample itself is not gathered into the spectroscope. Hence, the background and its variation can be reduced, thereby achieving an improvement of the analysis accuracy.

Further, formation of the sample holder section with a flat plate having a predetermined thickness makes it possible to gather into the spectroscope many spectral lines which are independent of the vapor cloud, so that the background and its variation can be reduced, thereby achieving an improvement of the analysis accuracy and an expansion of the lower determination limit as well.

As an analysis result, there is shown in TABLE 2 an example in which a carbon steel is selected as a sample, and N is determined. Incidentally, analysis conditions of Example-1 and Comparison-1 are as follows:

| Emission spectral analyzer: | PDA-5017 TYPE, by Shimadzu Corporation |
|---|---|
| Discharge conditions: | Voltage 330V, Capacitance 3 μF Inductance 10 μH, Discharge cycle 325 Hz |
| Emission stand: | Example-1/Horizontal emission stand (FIG. 1) Comparison-1/Ramp emission stand (FIG. 6) |

TABLE 2

| | | analysis conditions | |
|---|---|---|---|
| | | Example-1 Horizontal emission stand spectroscope: one (100–160 nm use) Wavelength: 149.2 nm | Comparison-1 Ramp emission stand spectroscope: one (100–160 nm use) Wavelength: 149.2 nm |
| number of times of analysis | 1st time | 0.0063 (%) | 0.0005 (%) |
| | 2nd time | 0.0064 | 0.0079 |
| | 3rd time | 0.0060 | 0.0042 |
| | 4th time | 0.0059 | 0.0054 |
| | 5th time | 0.0062 | 0.0068 |
| | average | 0.00616 (%) | 0.00656 (%) |
| | standard deviation (σ) | 0.00021 (%) | 0.00158 (%) |

It will be understood from TABLE 2 that Example-1 using the horizontal emission stand is improved in the analysis accuracy (standard deviation σ) about eight times comparing with Comparison-1.

EXAMPLES 2, 3 and COMPARISON 2

Figure 4:
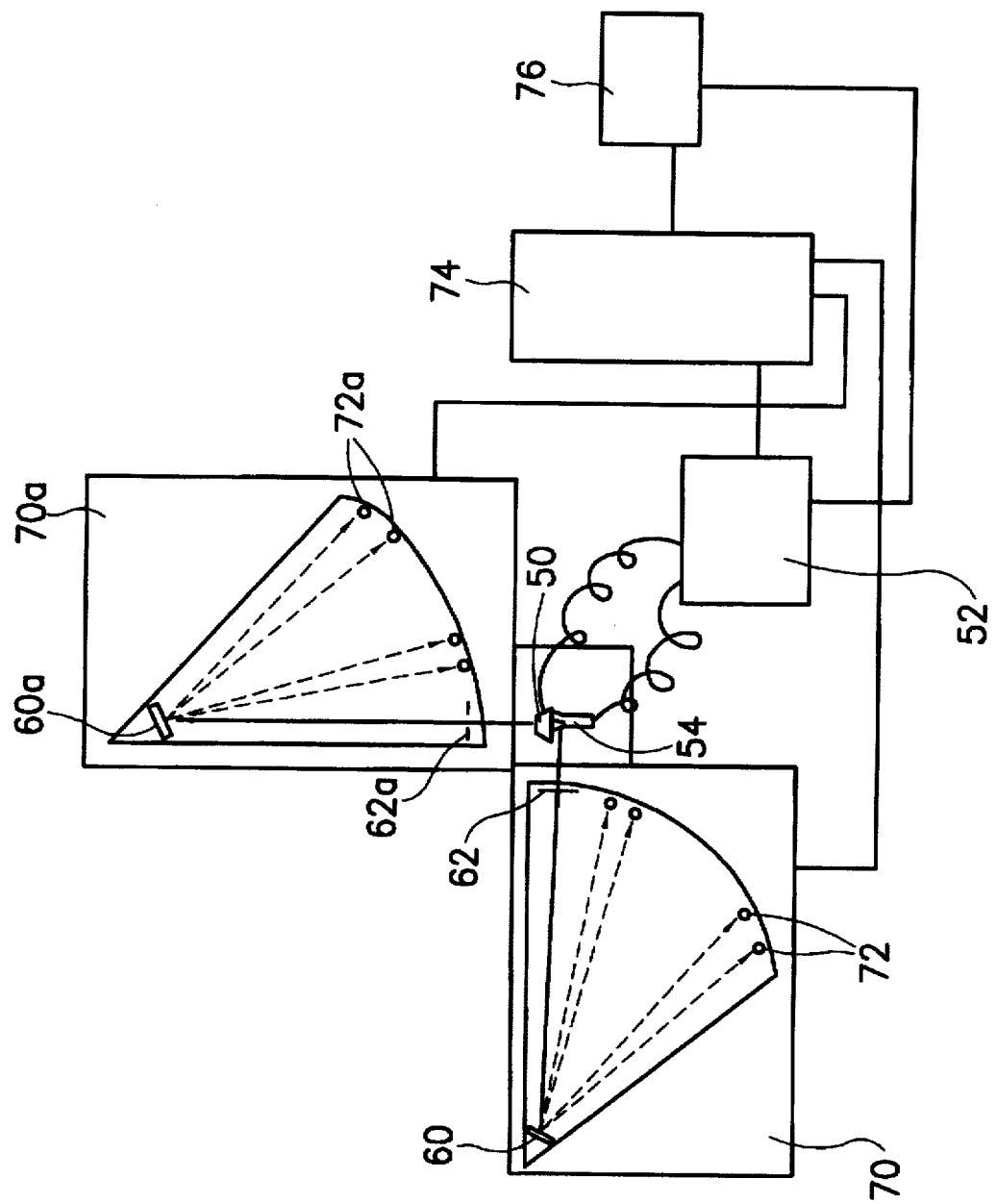
FIG. 4 is a schematic plan view of another emission spectral analyzer according to the present invention shown as a whole.
Figure 5:
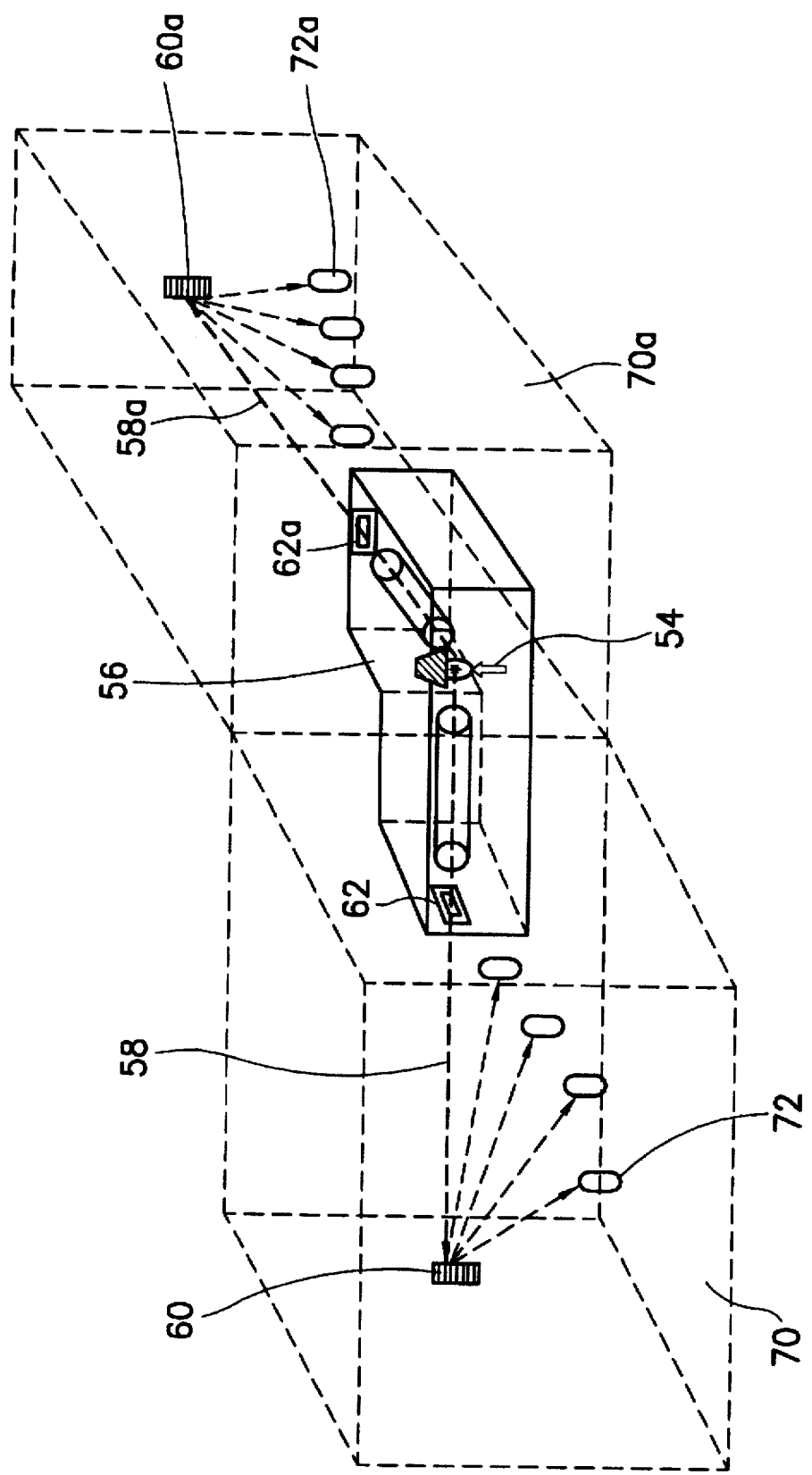
FIG. 5 is a perspective view showing typically an emission stand and a spectroscope of the emission spectral analyzer according to the present invention.

FIG. 4 shows by way of example an apparatus for practicing an emission spectral analysis method according to the present invention, in which, two spectroscopes 70 and 70a are disposed. In FIG. 4, a three-dimensional positional relationship between the emission stand and the spectroscope is one as shown in FIG. 5. Such an apparatus comprises: a discharge device 52; a emission section including an emission stand 56 consisting of a sample 50 and a counter electrode 54; spectroscopes 70 and 70a comprising diffraction gratings 60 and 60a, slits 62 and 62a, and spectral line detectors 72 and 72a, respectively; a photometric device 74 for performing an arithmetic processing on data through a digital conversion of analog amount of spectrum; and a content computer 76 for converting spectral line intensity to content. It is important that as to the emission stand 56, the surface of the sample 50 is made, as shown in FIG. 5, to be substantially parallel to light gathering axes 58 and 58a of the spectroscopes 70 and 70a. Because, if so arranged, components involved in the direction available for gathering into the spectroscopes 70 and 70a are increased, which is different from the conventional emission stand, as shown in FIG. 6, in which the surface of the sample 16 is inclined.

FIG. 5 is a perspective view showing typically an example of an arrangement of an emission stand 56 for use in analysis of a steel sample and spectroscopes 70 and 70a. According to this example, two spectroscopes 70 and 70a are disposed in such a positional relation that they are located apart each other at about 90 degree of angle looking in a plane view, so that light emanating from the sample 50 is introduced separately into the respective spectroscopes 70 and 70a.

Incidentally, if the slits 62 and 62a as shown in FIG. 5 are used to gather light through hierarchically partitioning the discharge section in a height direction, it is possible to analyze heavy elements and light elements with great accuracy, respectively, since the plasma section near the sample is involved in higher intensity of spectral lines of heavy elements, whereas the plasma section near the electrode is involved in higher intensity of spectral lines of light elements.

Actually, to analyze the sample 50, a discharge chamber of the emission stand 56 is brought into an atmosphere of the inert gas such as Ar or He, and a voltage is applied to a gap between the sample 50 and the counter electrode 54 to perform a spark discharge, thereby exciting the sample 50 to emit the spectral lines of the respective elements.

According to the present example, the spectroscope 70 is used for the purpose of diffracting and spectroscopically dispersing elements having 160 nm to 600 nm in the wavelength of the spectral line, and specifically, the elements, such as Si, Mn, P, S, Al, Cu, Ni, Cr, Mo, V, Nb, Ti, As, Na and the like, are of interest. On the other hand, the spectroscope 70a is used for the purpose of diffracting and spectroscopically dispersing elements having 100 nm to 160 nm in the wavelength of the spectral line, and specifically, the elements, such as O, N, C and the like, are of interest. The spectroscopes 70 and 70a are provided with detectors (photomultipliers) 72 and 72a each arranged in alignment every the associated wavelength, respectively, so that the inherent spectral line of each element spectroscopically dispersed can be trapped at the optimum position. The inherent spectral lines of the respective elements thus detected are simultaneously converted into emission intensity through the photometric device 74 shown in FIG. 4, and the converted emission intensity is fed to the content computer 76 and is subjected to an arithmetic processing to evaluate contents.

As an analysis result, there is shown in TABLE 3 an example in which a carbon steel is selected as a sample, and C is determined. Incidentally, analysis conditions of Example-2, Example-3, and Comparison-2 are as follows:

| | |
|---|---|
| Emission spectral analyzer: | Improvement of PDA-5017 TYPE, Shimadzu Corporation, as shown in FIGS. 4 and 5 |
| Discharge conditions: | Voltage 330V, Capacitance 3 μF, Inductance 10 μH, Discharge cycle 325 Hz |
| Emission stand: | Example-2/Horizontal type (FIG. 1) Example-3/Horizontal type (FIGS. 4, 5) Comparison-2/Ramp type (FIGS. 6, 7) |

As apparent from the above, providing a plurality of spectroscopes for each of a plurality of elements of interest in analysis makes it possible to simultaneously analyze all of the elements with great accuracy. Further, since there is no need of an exchanging work for the spectroscopes, a regulation of the light axis at exchange, which will take a half day, can be avoided. Thus, it is possible to contribute to a reduction of analysis time and the labor-saving for the analysis work.

Further, according to the present invention, it is possible to expand the lower determination limits of elements N and O to 5 ppm and 20 ppm, respectively, which cannot be analyzed with the conventional emission spectral analysis scheme. With respect to element C, the lower determination limit of the prior 20 ppm can be expanded to 3 ppm.

Industrial Applicability

As mentioned above, when analysis is performed by an emission spectral analysis method and apparatus according to the present invention:

(1) It is possible to use for a measurement the optimum spectral line wavelength for the element, thereby improving the analysis accuracy and in addition expanding the lower determination limit.

(2) Since all of the necessary elements can be measured, it is permitted to measure an amount of elements which have an effect on the measurement to correct it, even if it is subjected to interference on a spectroscopical dispersing basis (influence of overlap of the spectral lines). Thus, the analysis value is improved in accuracy.

(3) Since ultraviolet rays less than 150 nm can be measured, it becomes possible to determine the elements H, N, O.

(4) It becomes possible to perform a multi-element simultaneous determination, thereby reducing the time required for analysis.

As a result, it is possible to expect development of a high purity of metal, improvement in yield in a refining process and reduction of the manufacturing cost, and also to expect secondary effects such as reduction of working time, and saving of analyzing cost.

TABLE 3

| | | analysis conditions | | |
|---|---|---|---|---|
| | | Example-2 Horizontal emission stand spectroscope: one (160–600 nm use) Wavelength: 165.8 nm | Example-3 Horizontal emission stand spectroscope: two (160–600 nm use) (100–160 nm use) Wavelength: 156.1 nm | Comparison-2 Horizontal emission stand spectroscope: one (160–600 nm use) Wavelength 165.8 nm |
| number of times of analysis | 1st time | 0.0025 (%) | 0.0026 (%) | 0.0024 (%) |
| | 2nd time | 0.0025 | 0.0026 | 0.0028 |
| | 3rd time | 0.0026 | 0.0025 | 0.0025 |
| | 4th time | 0.0027 | 0.0025 | 0.0028 |
| | 5th time | 0.0025 | 0.0026 | 0.0025 |
| | average | 0.00256 (%) | 0.00256 (%) | 0.00260 (%) |
| | standard deviation ($\sigma$) | 0.00008 (%) | 0.00005 (%) | 0.00019 (%) |

It is apparent from TABLE 3 that Example-2 using the horizontal emission stand is improved in the analysis accuracy (standard deviation) about twice comparing with Comparison-2, and Example-3 using the horizontal emission stand including two spectroscopes is further improved in the analysis accuracy.

I claim:

1. In an emission spectral analysis method of metallic samples in which a discharge is caused between a sample and a counter electrode to emit light, the light thus emanated is gathered, and spectral lines peculiar to respective component elements included therein are spectroscopically dispersed, and wavelength and intensity on each of the inherent spectral lines are measured, the steps comprising:

gathering discharge light in such a manner that a surface of said sample does not come within the range of a spectroscope, wherein the light gathering is conducted on each of at least two kinds of wavelength area selected from the group consisting of (a) a wavelength area of an ultraviolet rays region less than 100 nm–160 nm, (b) a wavelength area of a visible rays region of 160 nm–600 nm, and (c) a wavelength area of an infrared rays region over 600 nm, conducting a spectroscopical dispersing, and measuring said component elements to a level on the order of 1 ppm.

2. In an emission spectral analysis method of metallic samples in which a discharge is caused between a sample and counter electrode to emit light, the light thus emanated is gathered and spectral lines peculiar to respective component elements included therein are spectroscopically dispersed, and wavelength and intensity on each of the inherent spectral lines are measured, the steps comprising:

keeping a surface of the sample facing the counter electrode with an inclination below 5° with respect to a light gathering axis of a spectroscope, gathering light from a plurality of directions, wherein the light gathering is conducted on each of at least two kinds of wavelength area selected from the group consisting of (a) a wavelength area of an ultraviolet rays region less than 100 nm–160 nm, (b) a wavelength area of a visible rays region of 160 nm–600 nm, and (c) a wavelength area of an infrared rays region over 600 nm, conducting a spectroscopical dispersing, and measuring said component elements to a level on the order of 1 ppm.

3. An emission spectral analysis method according to claim 2, wherein messages as to intensity of spectral lines peculiar to respective component elements obtained through light gathering from said plurality of directions are simultaneously measured and then converted into contents, and in addition correction of coexisting elements is also simultaneously performed.

4. An emission spectral analysis method according to claim 2, wherein said light gathering axis is made to be a straight line.

5. The method defined in claims 1 or 2 wherein said component elements are selected from the group consisting of Si, Mn, P, S, Al, Cu, Ni, Cr, Mo, V, Nb, Ti, As, Na, O, N and C.

6. An emission spectral analysis apparatus for metallic samples comprising:

an emission stand having a sample holder, a discharge device, two or more spectroscopes corresponding to a measurement of spectral lines of two or more wavelength areas selected from the group consisting of (a) a wavelength area of an ultraviolet rays region less than 100 nm–160 nm, (b) a wavelength area of a visible rays region of 160 nm–600 nm, and (c) a wavelength area of an infrared rays region over 600 nm, wherein the content of component elements in said metallic samples are measured on the order of 1 ppm, a photometric device, and a content computer, wherein the inclination of a light gathering axis of said spectroscopes with respect to a sample holding surface on said sample holder is below 5°.

7. An emission spectral analysis apparatus according to claim 6, wherein said sample holder is a flat plate having a thickness of not less than one sixth and not more than one third of a length between a sample held by said sample holder and a tip of said discharge device.

8. An emission spectral analysis apparatus according to claim 6, wherein a sample holding section of said sample holder, which comes in contact with a sample, is constituted of a flat plate having a thickness of not less than one sixth and not more than one third of a length between the sample and a tip of said discharge device.

9. An emission spectral analysis apparatus according to claim 6 or 8, wherein the sample holder is made of ceramics, and said sample holding surface is provided with a metallic coating.

10. An emission spectral analysis apparatus for metallic samples comprising:

an emission stand, a discharge device, a photometric device, and a content computer, two or more spectroscopes corresponding to a measurement of spectral lines of two or more wavelength areas selected from the group consisting of (a) a wavelength area of an ultraviolet rays region less than 100 nm–160 nm, (b) a wavelength area of a visible rays region of 160 nm–600 nm, and (c) a wavelength area of an infrared rays region over 600 nm, wherein said emission stand has a sample holding section in which inclination of a light gathering axis of said spectroscopes with respect to a sample holding surface of said sample holding section facing said discharge device is below 5°; and wherein the content of component elements in said metallic samples are measured on the order of 1 ppm.

11. The method defined in claims 6 or 10 wherein said component elements are selected from the group consisting of Si, Mn, P, S, Al, Cu, Ni, Cr, Mo, V, Nb, Ti, As, Na, O, N and C.

* * * * *